US 8,974,708 B2

(12) United States Patent
Shintou et al.

(10) Patent No.: US 8,974,708 B2
(45) Date of Patent: Mar. 10, 2015

(54) COLORING MATTER COMPOUND, INK, RESIST COMPOSITION FOR COLOR FILTER, AND HEAT-SENSITIVE TRANSFER RECORDING SHEET

(71) Applicant: Canon Kabushiki Kaisha, Tokyo (JP)

(72) Inventors: Taichi Shintou, Saitama (JP); Yuko Katsumoto, Yokohama (JP); Akiko Kitao, Kawasaki (JP); Takeshi Miyazaki, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/182,982

(22) Filed: Feb. 18, 2014

(65) Prior Publication Data

US 2014/0158956 A1     Jun. 12, 2014

Related U.S. Application Data

(63) Continuation of application No. PCT/JP2013/005046, filed on Aug. 27, 2013.

(30) Foreign Application Priority Data

Aug. 29, 2012    (JP) ................... 2012-188149

(51) Int. Cl.
*G02B 5/23*     (2006.01)
*B41J 31/00*    (2006.01)
(Continued)

(52) U.S. Cl.
CPC . *G02B 5/23* (2013.01); *B41J 31/00* (2013.01); *C09B 23/00* (2013.01); *C09D 11/00* (2013.01);
(Continued)

(58) Field of Classification Search
USPC .......... 252/586; 544/105, 131, 148, 149, 171, 544/174, 193, 194, 256, 261, 270.7, 276.4, 544/277.1, 277.4, 278.7, 281.4; 546/270.7
See application file for complete search history.

(56) References Cited

U.S. PATENT DOCUMENTS 5,369,078 A    11/1994 Eguchi et al.
5,550,098 A    8/1996 Aso et al.
(Continued)

FOREIGN PATENT DOCUMENTS

JP    5-262062 A    10/1993
(Continued)

OTHER PUBLICATIONS

International Search Report in Application No. PCT/JP2013/005046 (mailed Oct. 1, 2013).
Written Opinion in Application No. PCT/JP2013/005046 (mailed Oct. 1, 2013).

*Primary Examiner* — Bijan Ahvazi
(74) *Attorney, Agent, or Firm* — Fitzpatrick, Cella, Harper & Scinto

(57) ABSTRACT

The coloring matter compound is represented by the following general formula (1):

General formula (1)

wherein $R_1$, $R_2$, $R_6$ represent an alkyl group; $R_3$ to $R_5$ represent an alkyl group, or satisfy either of the following conditions i) and ii): i) $R_3$ and $R_4$ are bonded to each other, so as to form a cyclic organic functional group containing $R_3$, $R_4$ and a carbon atom bonded to $R_3$ and $R_4$, and $R_5$ represents an alkyl group; ii) $R_3$ to $R_5$ are bonded to one another, so as to form a cyclic organic functional group containing $R_3$, $R_4$, $R_5$ and a carbon atom bonded to $R_3$ to $R_5$; and $R_7$, $R_8$ represent an alkyl group or an acyl group, or $R_7$ and $R_8$ are bonded to each other, so as to form a cyclic organic functional group containing $R_7$, $R_8$ and a nitrogen atom bonded simultaneously to $R_7$ and $R_8$.

7 Claims, 1 Drawing Sheet

(51) Int. Cl.
*C09B 23/00* (2006.01)
*C09D 11/00* (2014.01)
*G03F 7/004* (2006.01)
*B41M 5/26* (2006.01)
*C07D 417/06* (2006.01)
*B41M 5/385* (2006.01)
*G03F 7/00* (2006.01)
*G03F 7/105* (2006.01)
*C07D 417/00* (2006.01)

(52) U.S. Cl.
CPC ............... *G03F 7/004* (2013.01); *B41M 5/265* (2013.01); *C07D 417/06* (2013.01); *B41M 5/385* (2013.01); *G03F 7/0007* (2013.01); *G03F 7/105* (2013.01)
USPC ........................................ 252/586; 546/270.7

(56) References Cited

U.S. PATENT DOCUMENTS

| | | | |
|---|---|---|---|
| 5,580,980 A * | 12/1996 | Etzbach et al. | 544/105 |
| 5,607,895 A | 3/1997 | Eguchi et al. | |
| 5,654,122 A | 8/1997 | Etzbach et al. | |
| 5,785,719 A * | 7/1998 | Etzbach et al. | 8/471 |
| 6,528,223 B1 | 3/2003 | Wilson et al. | |

FOREIGN PATENT DOCUMENTS

| | | |
|---|---|---|
| JP | 7-502545 A | 3/1995 |
| JP | 10-508047 A | 8/1998 |
| JP | 2003-195570 A | 7/2003 |
| JP | 2003-344998 A | 12/2003 |
| WO | 92/19684 A1 | 11/1992 |
| WO | 2014/034093 A1 | 3/2014 |

* cited by examiner

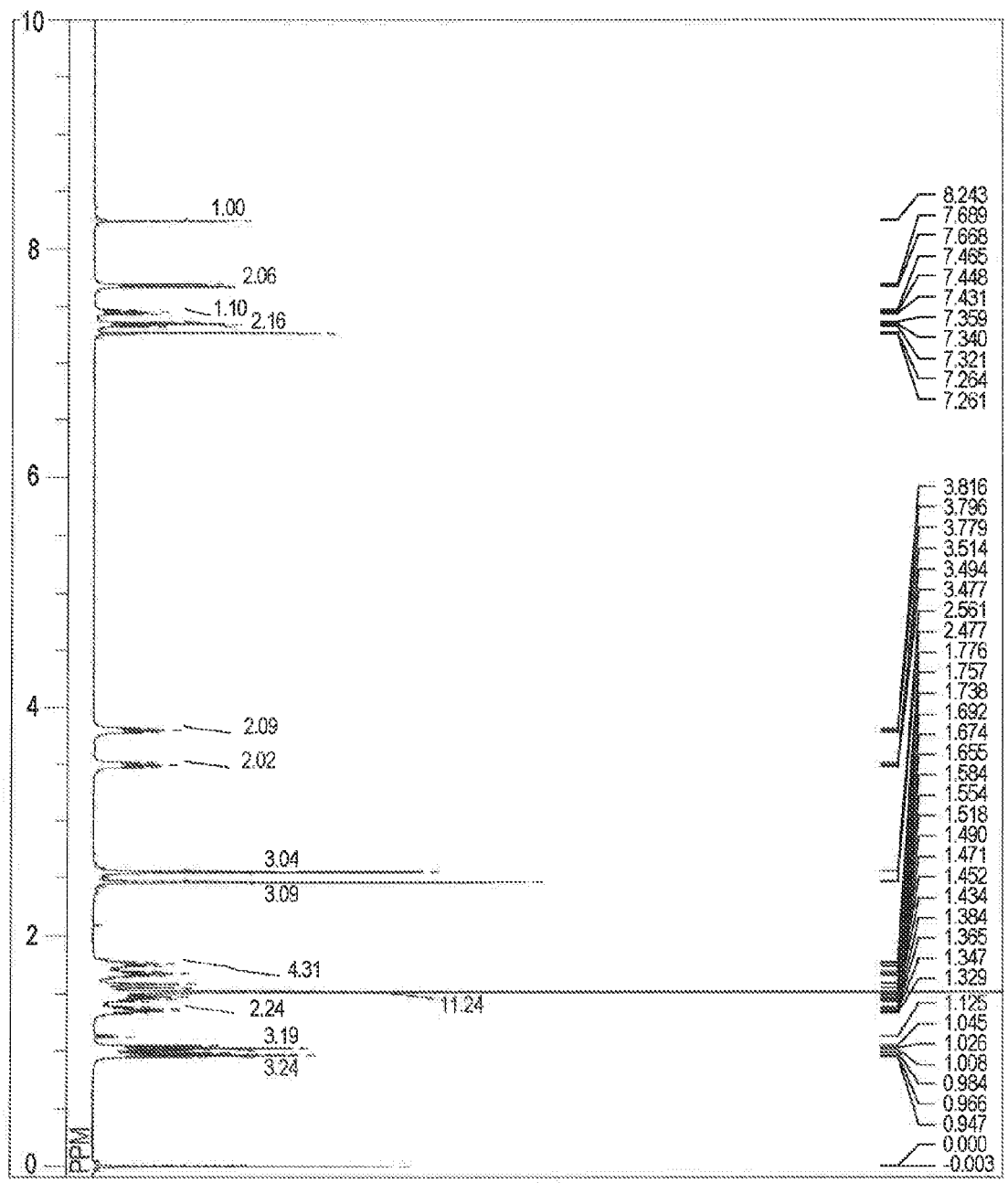

COLORING MATTER COMPOUND, INK, RESIST COMPOSITION FOR COLOR FILTER, AND HEAT-SENSITIVE TRANSFER RECORDING SHEET

CROSS-REFERENCE TO RELATED APPLICATIONS

This application is a continuation of International Application No. PCT/JP2013/005046, filed Aug. 27, 2013, which claims the benefit of Japanese Patent Application No. 2012-188149, filed Aug. 29, 2012.

BACKGROUND OF THE INVENTION

1. Field of the Invention

The present invention relates to a coloring matter compound, and an ink, a resist composition for a color filter and a heat-sensitive transfer recording sheet all containing the coloring matter compound.

2. Description of the Related Art

Recently, there have been increasing demands for image quality improvement for color images in a color liquid crystal display and the like. A color filter is indispensable for color display in a liquid crystal display and is a significant component that affects the performance of the liquid crystal display. As a conventional method for producing a color filter, a dyeing method, a printing method, an inkjet method, and a photoresist method are known. Among these methods, production by the photoresist method is principally employed because in this method, spectral properties and color reproducibility can be easily controlled and resolution is so high that high resolution patterning can be performed.

In the photoresist method, a pigment has been generally used as a coloring agent, but there are a large number of problems such as depolarization (namely, disturbance of polarization), lowering of a contrast ratio in color display in a liquid crystal display, lowering of brightness of a color filter, and stabilization of dispersion in an organic solvent or a polymer. Therefore, attention is now being paid to a production method using a dye. For example, in order that an image with good spectral properties and a high display contrast can be displayed, a color filter using, as a coloring agent, a xanthene coloring matter has been reported (see Japanese Patent Application Laid-Open No. 2003-344998). In order to display an image with higher resolution, however, it is desired to develop a color filter with strong light resistance and good spectral properties.

Moreover, coloring matter compounds are desired to be improved in fields other than the field of color filters. An example of such fields includes a field of an image formation method employing a heat-sensitive transfer recording method.

The heat-sensitive transfer recording method is an image formation method by which recording is performed as follows: A heat-sensitive transfer sheet formed on a sheet-shaped substrate and including a coloring material layer containing a thermally migratory coloring matter is overlaid on an image receiving sheet having, on a surface thereof, a coloring matter receiving layer, and the heat-sensitive transfer sheet is heated so as to transfer the coloring matter contained in the heat-sensitive transfer sheet onto the image receiving sheet. In this heat-sensitive transfer recording method, a coloring matter compound contained in a transfer sheet and an ink composition for the transfer sheet is an extremely significant material because this compound affects the speed of the transfer recording, image quality of recorded products, and storage stability. As a coloring matter to be used in this heat-sensitive transfer recording method, use of methine coloring matters excellent in clarity, color reproducibility, coloring density and the like has been reported (see International Application No. WO 92/19684 and Japanese Patent Application Laid-Open No. H05-262062). These dyes have, however, a problem in which the light resistance is low, and even now, a coloring matter compound having further improved light resistance is desired to be developed.

SUMMARY OF THE INVENTION

An object of the present invention is to provide a coloring matter compound excellent in light resistance. Another object of the present invention is to provide an ink, a resist composition for a color filter and a heat-sensitive transfer recording sheet all excellent in light resistance.

The aforementioned objects can be achieved by using the following coloring matter compound.

The present invention relates to a coloring matter compound represented by the following general formula (1):

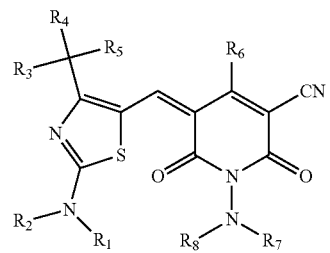

General formula (1)

wherein $R_1$, $R_2$ and $R_6$ each independently represent an alkyl group; $R_3$ to $R_5$ each independently represent an alkyl group, or satisfy either of the following conditions i) and ii): i) $R_3$ and $R_4$ are bonded to each other, so as to form a cyclic organic functional group containing $R_3$, $R_4$ and a carbon atom bonded simultaneously to $R_3$ and $R_4$, and $R_5$ represents an alkyl group; and ii) $R_3$ to $R_5$ are bonded to one another, so as to form a cyclic organic functional group containing $R_3$, $R_4$, $R_5$ and a carbon atom bonded simultaneously to $R_3$ to $R_5$; and $R_7$ and $R_8$ each independently represent an alkyl group or an acyl group, or $R_7$ and $R_8$ are bonded to each other, so as to form a cyclic organic functional group containing $R_7$, $R_8$ and a nitrogen atom bonded simultaneously to $R_7$ and $R_8$.

Furthermore, the present invention relates to an ink containing the above-described coloring matter compound, and a medium for dissolving or dispersing the coloring matter compound therein.

Moreover, the present invention relates to a resist composition for a color filter containing the above-described coloring matter compound.

Furthermore, the present invention relates to a heat-sensitive transfer recording sheet containing a substrate, and a coloring material layer formed on the substrate and containing the above-described coloring matter compound.

According to the present invention, a coloring matter compound excellent in light resistance can be provided. Besides, an ink, a resist composition for a color filter and a heat-sensitive transfer recording sheet all excellent in light resistance can be provided.

Further features of the present invention will become apparent from the following description of exemplary embodiments with reference to the attached drawings.

BRIEF DESCRIPTION OF THE DRAWINGS

FIGURE is a diagram of a $^1$H-NMR spectrum of a compound (1), that is, one of coloring matter compounds of the present invention represented by the general formula (1), obtained in $CDCl_3$ at room temperature at 400 MHz.

DESCRIPTION OF THE EMBODIMENTS

The present invention will now be described in more details.

As a result of earnest studies made for solving the aforementioned problems, the present inventors have found that not a thiazole ring having an unsubstituted phenyl group at the 4-position described in conventional technique but a coloring matter compound represented by the following general formula (1) is excellent in light resistance. The present inventors also found that the coloring matter compound can be used for obtaining an ink, a resist composition for a color filter and a heat-sensitive transfer recording sheet all of which are excellent in light resistance, and thus, the present invention was accomplished.

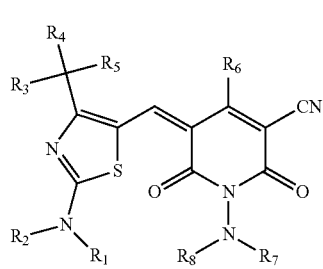

General formula (1)

wherein $R_1$, $R_2$ and $R_6$ each independently represent an alkyl group; $R_3$ to $R_5$ each independently represent an alkyl group, or satisfy either of the following conditions i) and ii): i) $R_3$ and $R_4$ are bonded to each other, so as to form a cyclic organic functional group containing $R_3$, $R_4$ and a carbon atom bonded simultaneously to $R_3$ and $R_4$, and $R_5$ represents an alkyl group; and ii) $R_3$ to $R_5$ are bonded to one another, so as to form a cyclic organic functional group containing $R_3$, $R_4$, $R_5$ and a carbon atom bonded simultaneously to $R_3$ to $R_5$; and $R_3$ and $R_5$ each independently represent an alkyl group or an acyl group, or $R_7$ and $R_8$ are bonded to each other, so as to form a cyclic organic functional group containing $R_7$, $R_8$ and a nitrogen atom bonded simultaneously to $R_7$ and $R_8$.

First, the coloring matter compound represented by the general formula (1) will be described.

The alkyl group as $R_1$ and $R_2$ of the general formula (1) is not especially limited, but examples include primary, secondary or tertiary, saturated or unsaturated, straight-chain, branched or cyclic alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methyl cyclohexyl group, a 2-ethylpropyl group, a 2-ethylhexyl group, and a cyclohexenylethyl group. In particular, a branched alkyl group such as a 2-ethylhexyl group can be used because excellent light resistance can be thus attained.

The alkyl group as $R_3$ to $R_5$ of the general formula (1) is not especially limited, but examples include alkyl groups having 1 to 4 carbon atoms, such as a methyl group, an ethyl group, an n-propyl group, an iso-propyl group, and an n-butyl group. In particular, a methyl group can be used because excellent light resistance can be thus attained.

The cyclic organic functional group formed in the general formula (1) by a bond of $R_3$ and $R_4$ and containing $R_3$, $R_4$ and a carbon atom simultaneously bonded to $R_3$ and $R_4$ is not especially limited, but examples include polycyclic or monocyclic saturated cyclic hydrocarbon rings such as a cyclohexyl group and a cycloheptyl group.

The cyclic organic functional group formed by a bond of $R_3$ to $R_5$ and containing $R_3$, $R_4$, $R_5$ and a carbon atom simultaneously bonded to $R_3$ to $R_5$ is not especially limited, but an example includes an adamantyl group.

The alkyl group as $R_6$ of the general formula (1) is not especially limited, but examples include alkyl groups such as a methyl group, an ethyl group, an n-propyl group, an iso-propyl group, an n-butyl group, an iso-butyl group, a 2-methylbutyl group, a 2,3,3-trimethylbutyl group, and an octyl group. In particular, an alkyl group such as a methyl group, an n-butyl group, a 2-methylbutyl group, or a 2,3,3-trimethylbutyl group can be used because excellent light resistance can be thus attained.

The alkyl group as $R_7$ and $R_8$ of the general formula (1) is not especially limited, but examples include primary, secondary or tertiary, saturated or unsaturated, straight-chain, branched or cyclic alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methyl cyclohexyl group, a 2-ethylpropyl group, a 2-ethylhexyl group, and a cyclohexenylethyl group.

The acyl group as $R_7$ and $R_8$ of the general formula (1) is not especially limited, but examples include a formyl group, a substituted or unsubstituted alkyl carbonyl group having 2 to 30 carbon atoms, a substituted or unsubstituted aryl carbonyl group having 7 to 30 carbon atoms, and a hetero ring carbonyl group. Specific examples include an acetyl group, a propionyl group, a pivaloyl group, a benzoyl group, a naphthoyl group, a 2-pyridylcarbonyl group, and a 2-furylcarbonyl group.

The cyclic organic functional group formed in the general formula (1) by a bond of $R_7$ and $R_8$ and containing $R_7$, $R_8$ and a nitrogen atom simultaneously bonded to $R_7$ and $R_8$ is not especially limited, but examples include a piperidinyl group, a piperazinyl group and a morpholinyl group.

In particular, at least one of $R_7$ and $R_8$ can be an alkyl group because excellent light resistance can be thus attained. In this case, the alkyl group can be a methyl group because excellent light resistance can be thus attained.

The coloring matter compound of the present invention represented by the general formula (1) can be synthesized by referring to a known method described in International Application No. WO92/19684.

An embodiment of a preparation method for the coloring matter compound represented by the general formula (1) will now be described, but the preparation method is not limited to the following.

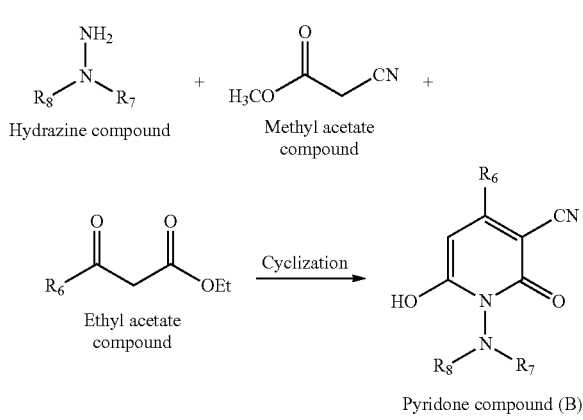

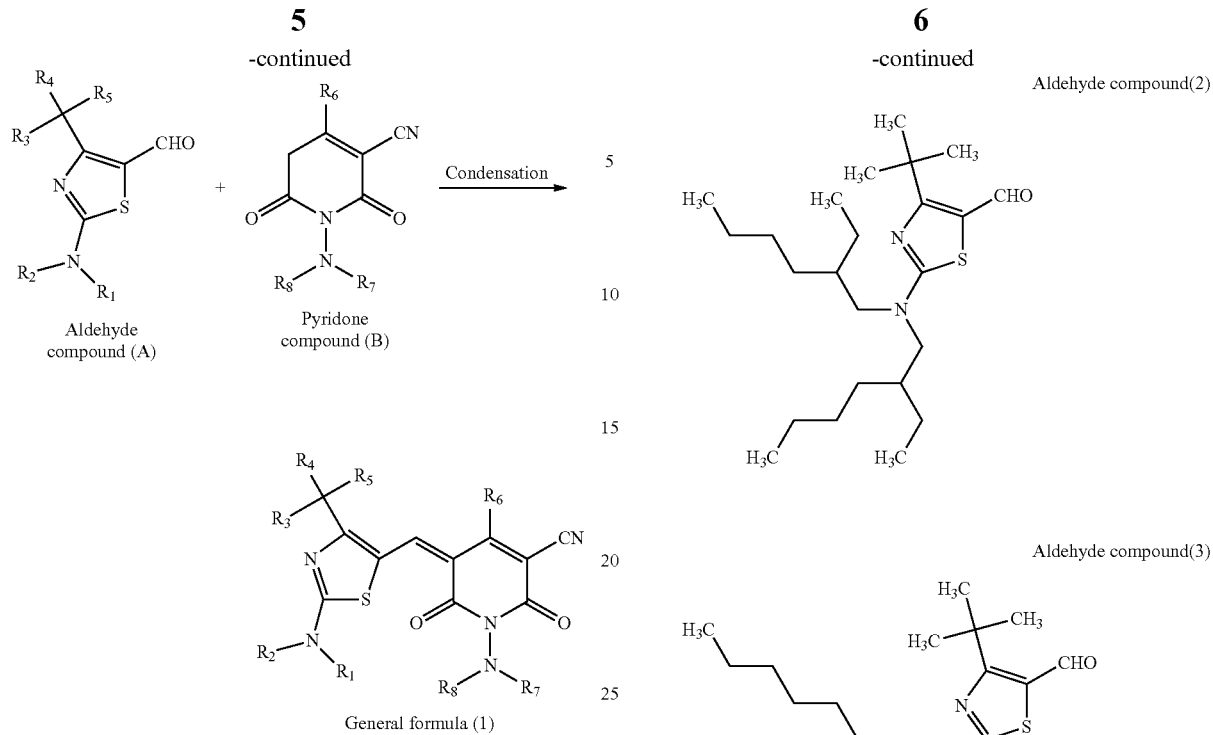

Incidentally, $R_1$ to $R_3$ of the compounds and the coloring matter compound represented by the general formula (1) in the aforementioned reaction formulas are the same as those defined above. Besides, the compound of the general formula (1) has cis-trans isomers, which also fall under the scope of the present invention. Furthermore, although the pyridone compound (B) has different structures in the aforementioned two reaction formulas, these compounds are isomers in an equilibrium relationship, and are substantially the same compound.

The coloring matter compound of the present invention can be prepared by condensing the aldehyde compound (A) and the pyridone compound (B).

The aldehyde compound (A) used in the present invention can be synthesized by referring to the known method described in International Application No. WO92/19684.

Suitable examples of the aldehyde compound (A) include, but are not limited to, the following aldehyde compounds (1) to (13):

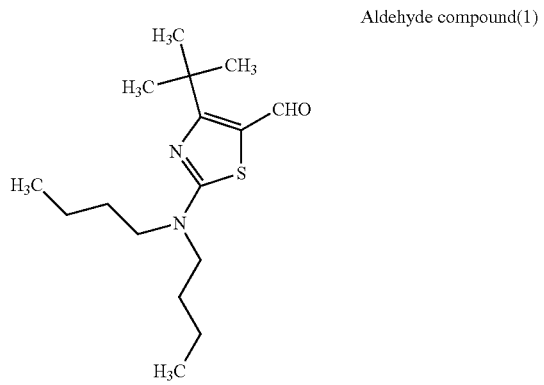

Aldehyde compound(1)

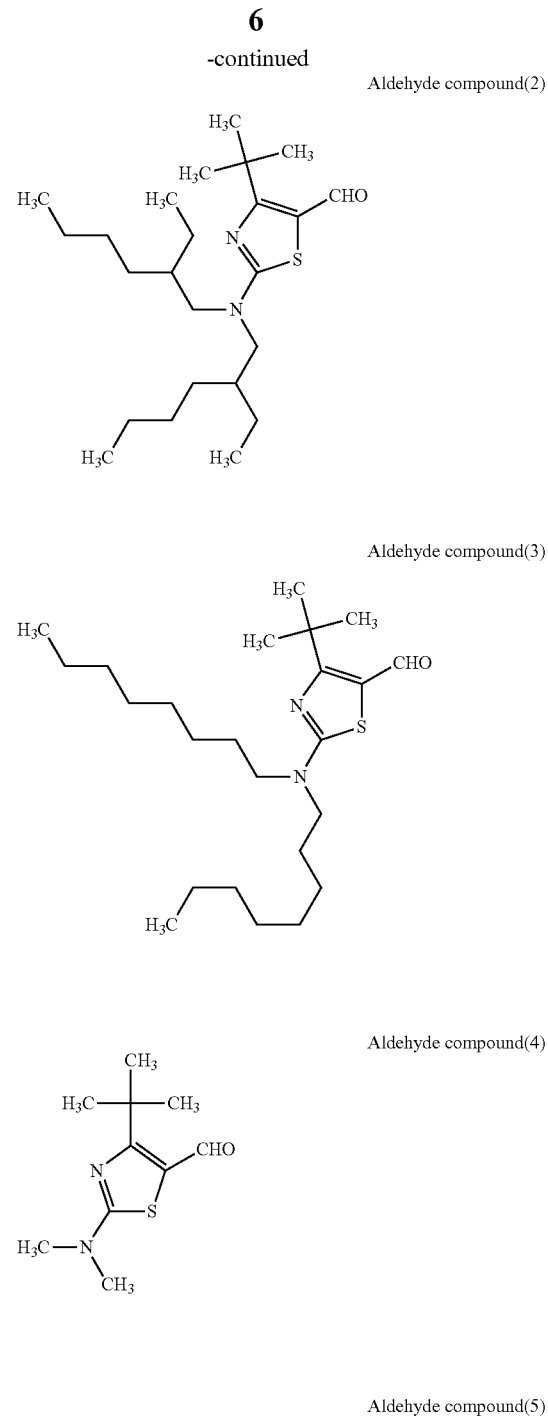

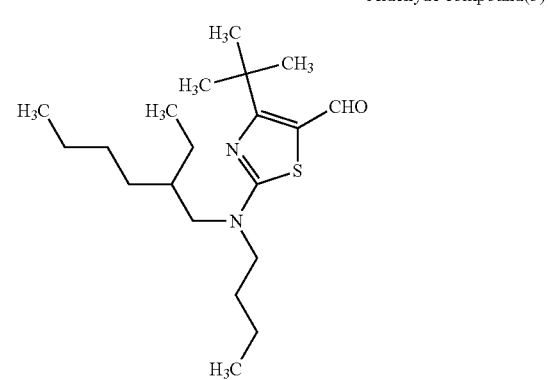

Aldehyde compound(5)

Aldehyde compound(6)

Aldehyde compound(7)

Aldehyde compound(8)

Aldehyde compound(9)

Aldehyde compound(10)

Aldehyde compound(11)

Aldehyde compound(12)

Aldehyde compound(13)

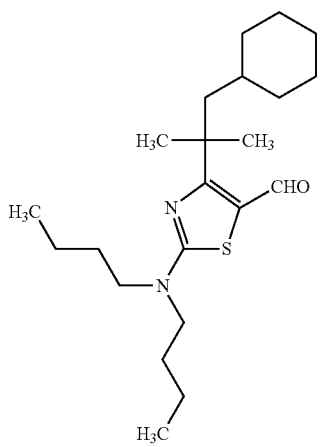

First, cyclization performed for obtaining the pyridone compound (B) will be described.

The pyridone compound (B) can be synthesized by cyclization for coupling three components, that is, a hydrazine compound, a methyl acetate compound and an ethyl acetate compound.

This cyclization can be performed with no solvent used, but is preferably performed in the presence of a solvent. The solvent is not especially limited as long as the solvent is not involved in the reaction, and examples include water, methanol, ethanol, acetic acid and toluene. Alternatively, a mixture of two or more solvents can be used, and a mixing ratio of the mixture can be arbitrarily determined. The amount of the reaction solvent used is preferably 0.1 to 1000% by mass, and more preferably 1.0 to 150% by mass based on the amount of the methyl acetate compound.

Since the reaction can proceed rapidly using a base in this cyclization, a base can be suitably used. Examples of a usable base specifically include: organic bases such as pyridine, 2-methylpyridine, diethylamine, diisopropylamine, triethylamine, piperidine, phenylethylamine, isopropylethylamine, methylaniline, 1,4-diazabicyclo[2.2.2]octane, tetrabutyl ammonium hydroxide, 1,8-diazabicyclo[5.4.0]undecene, and potassium acetate; organic metals such as n-butyl lithium and tert-butyl magnesium chloride; inorganic bases such as sodium borohydride, metallic sodium, potassium hydride, and calcium oxide; and metal alkoxides such as potassium tert-butoxide, sodium tert-butoxide, and sodium ethoxide. Among these bases, triethylamine or piperidine is preferably used, and triethylamine is more preferably used. The amount of the base used is preferably 0.01 to 100% by mass, more preferably 0.1 to 20% by mass and further more preferably 0.5 to 5% by mass based on the amount of the methyl acetate compound. After completing the reaction, a reaction product is purified by distillation, recrystallization or silica gel chromatography, and thus, a desired pyridone compound can be obtained.

Suitable examples of the pyridone compound (B) include, but are not limited to, the following pyridone compounds (1) to (15):

Pyridone compound(1)

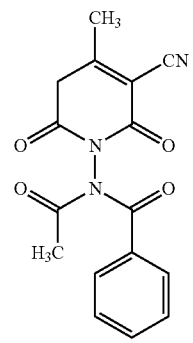

Pyridone compound(2)

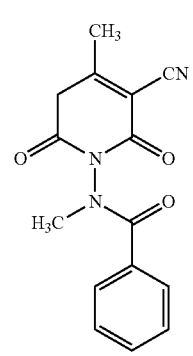

Pyridone compound(3)

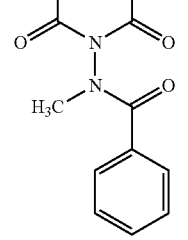

Pyridone compound(4)

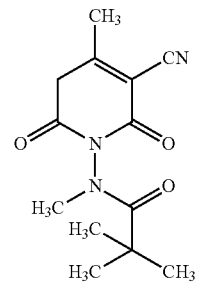

Pyridone compound(5)

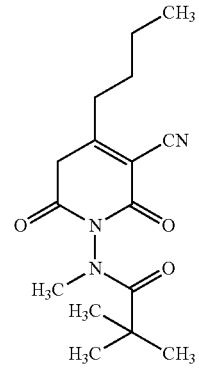

Pyridone compound(6)
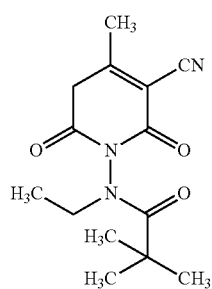
Pyridone compound(7)
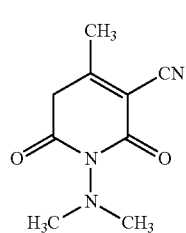
Pyridone compound(8)
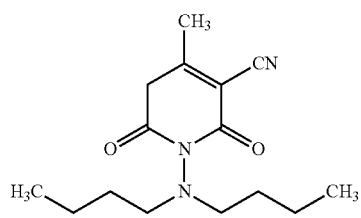
Pyridone compound(9)
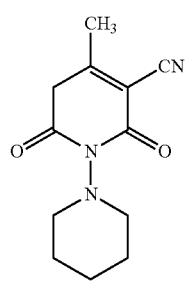
Pyridone compound(10)
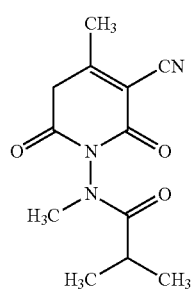
Pyridone compound(11)
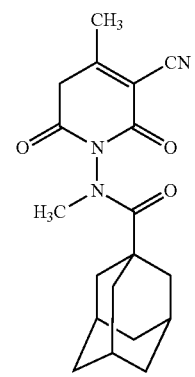
Pyridone compound(12)
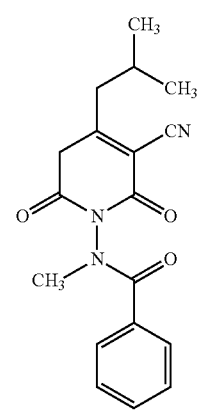
Pyridone compound(13)
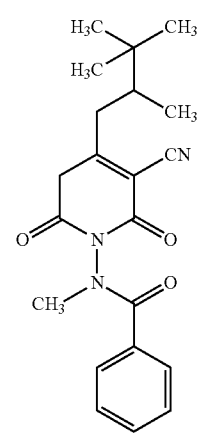
Pyridone compound(14)
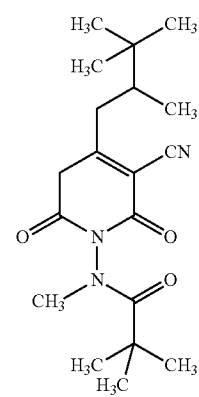

Pyridone compound(15)

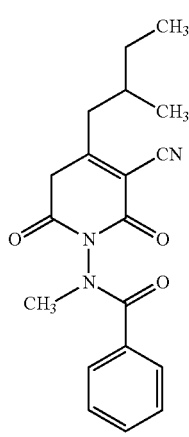

Next, condensation performed for obtaining the coloring matter compound represented by the general formula (1) of the present invention will be described.

The coloring matter compound represented by the general formula (1) of the present invention can be synthesized by condensation for condensing the aldehyde compound (A) and the pyridone compound (B).

This condensation can be performed with no solvent used, but is preferably performed in the presence of a solvent. The solvent is not especially limited as long as the solvent is not involved in the reaction, and examples include chloroform, dichloromethane, N,N-dimethylformamide, toluene, xylene, tetrahydrofuran, dioxane, acetonitrile, ethyl acetate, methanol, ethanol, isopropanol, and tetrahydrofuran. Alternatively, a mixture of two or more solvents can be used, and a mixing ratio of the mixture can be arbitrarily determined. The amount of the reaction solvent used is preferably 0.1 to 1000% by mass, and more preferably 1.0 to 150% by mass based on the amount of the aldehyde compound.

The reaction temperature of the condensation is preferably −80° C. to 250° C., and more preferably −20° C. to 150° C. The reaction of this condensation is generally completed within 24 hours.

An acid or a base can be used in this condensation because the reaction can thus proceed rapidly.

Examples of a usable acid specifically include inorganic acids such as hydrochloric acid, sulfuric acid and phosphoric acid; organic acids such as p-toluenesulfonic acid, formic acid, acetic acid, propionic acid, and trifluoroacetic acid; and organic acid salts such as ammonium formate and ammonium acetate. Among these, p-toluenesulfonic acid, ammonium formate and ammonium acetate can be suitably used. The amount of the acid used is preferably 0.01 to 20% by mass and more preferably 0.1 to 5% by mass based on the amount of the aldehyde compound.

Examples of a usable base specifically include: organic bases such as pyridine, 2-methylpyridine, diethylamine, diisopropylamine, triethylamine, piperidine, phenylethylamine, isopropylethylamine, methylaniline, 1,4-diazabicyclo[2.2.2]octane, tetrabutyl ammonium hydroxide, 1,8-diazabicyclo[5.4.0]undecene, and potassium acetate; organic metals such as n-butyl lithium and tert-butyl magnesium chloride; inorganic bases such as sodium borohydride, metallic sodium, potassium hydride, and calcium oxide; and metal alkoxides such as potassium tert-butoxide, sodium tert-butoxide, and sodium ethoxide. Among these bases, triethylamine or piperidine is preferably used, and triethylamine is more preferably used. The amount of the base used is preferably 0.1 to 20% by mass and more preferably 0.2 to 5% by mass based on the amount of the aldehyde compound.

The coloring matter compound represented by the general formula (1) thus obtained is subjected to an aftertreatment performed in a general organic synthesis, and thereafter, is purified by separation, recrystallization, reprecipitation, and column chromatography, and thus, a coloring matter compound with high purity can be obtained.

As the coloring matter compound represented by the general formula (1) in the present invention, one of such compounds may be singly used, or two or more of the compounds may be used in combination in order to adjust the color tone and the like according to the purpose of application. Furthermore, two or more of known pigments or dyes may be used together.

Preferable examples of the coloring matter compound of the present invention include, but are not limited to, the following compounds (1) to (25):

Compound (1)

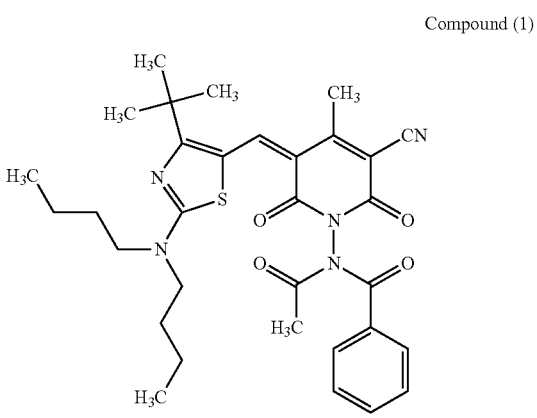

Compound (2)

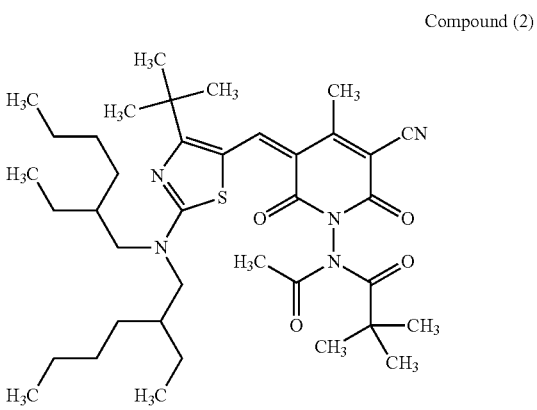

-continued
Compound (3)
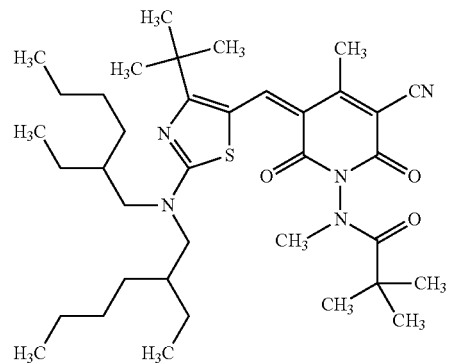
Compound (4)
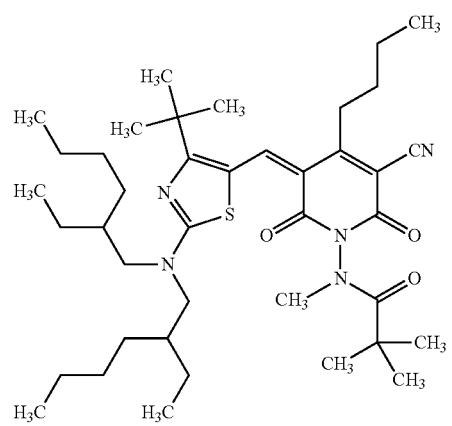
Compound (5)
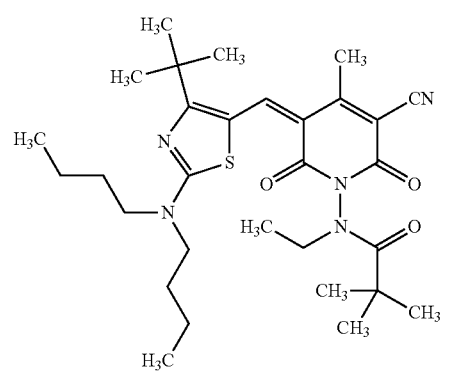
Compound (6)
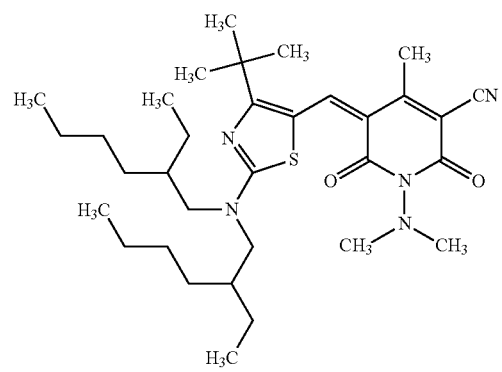
Compound (7)
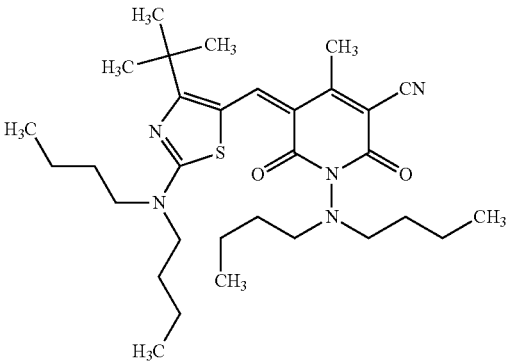
Compound (8)
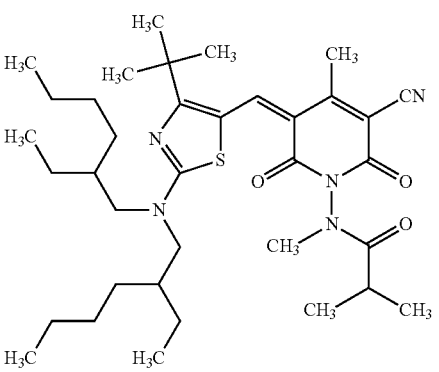
Compound (9)
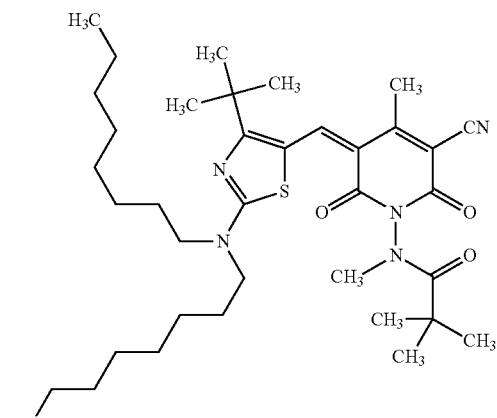
Compound (10)
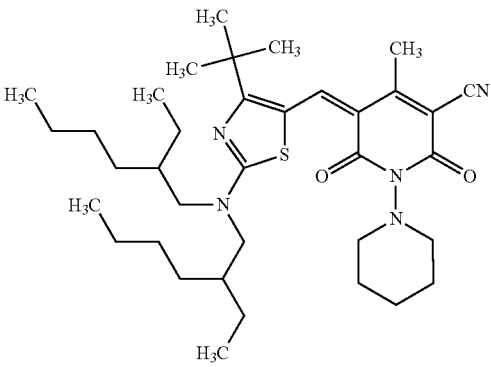

Compound (11)
Compound (12)
Compound (13)
Compound (14)
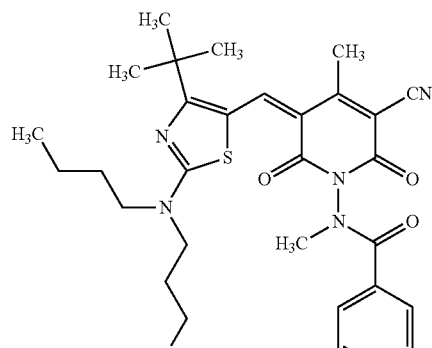
Compound (15)
Compound (16)
Compound (17)
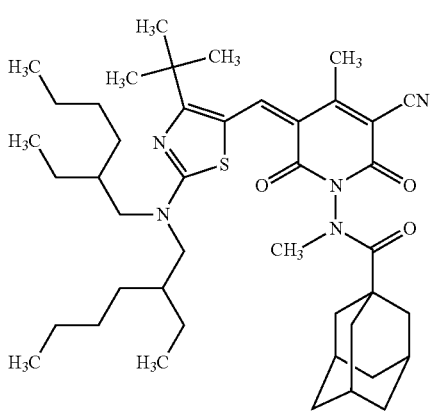
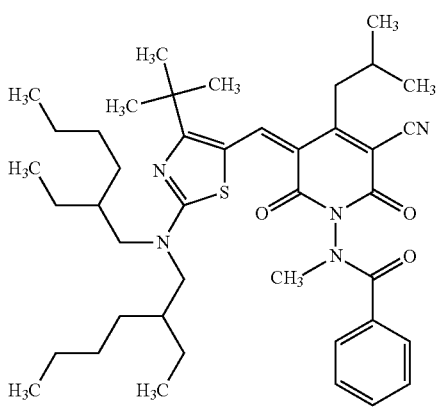
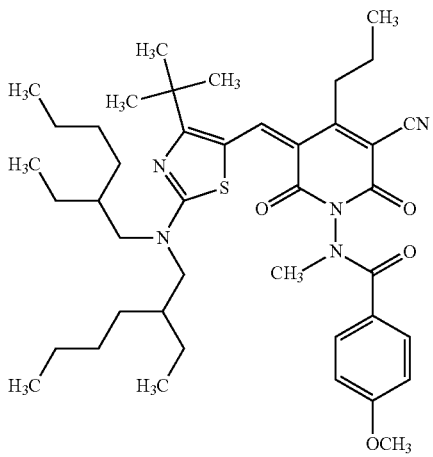

Compound (18)
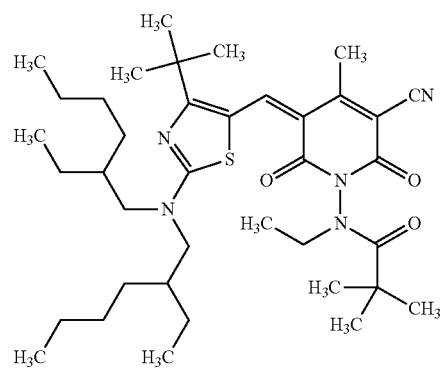
Compound (19)
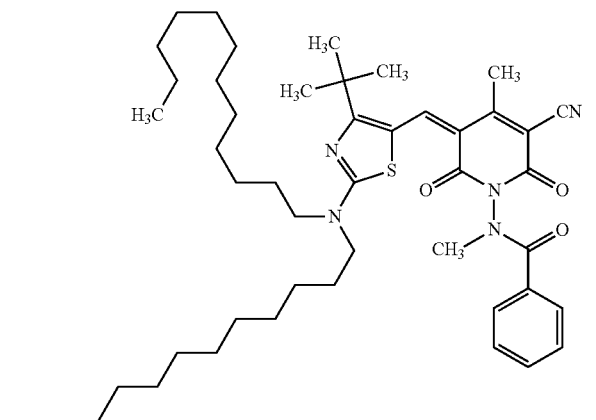
Compound (20)
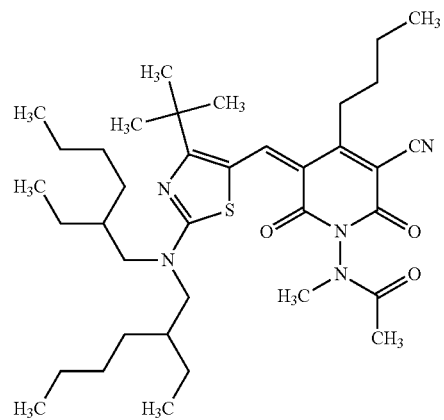
Compound (21)
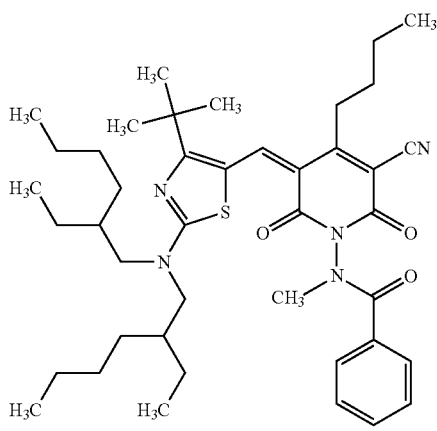
Compound (22)
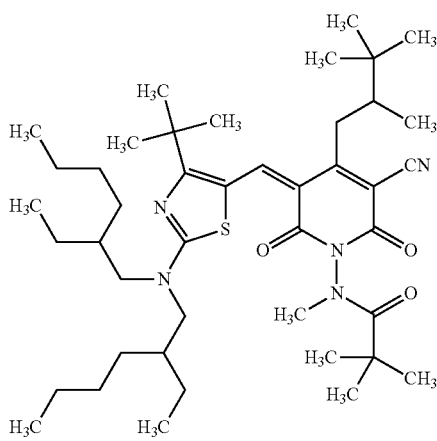
Compound (23)
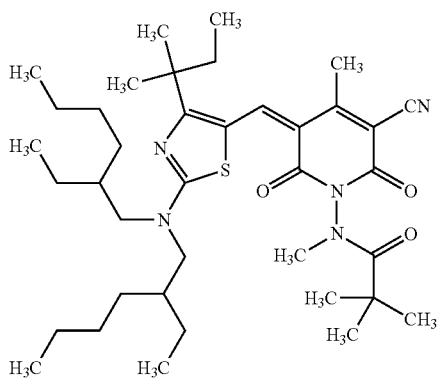

-continued

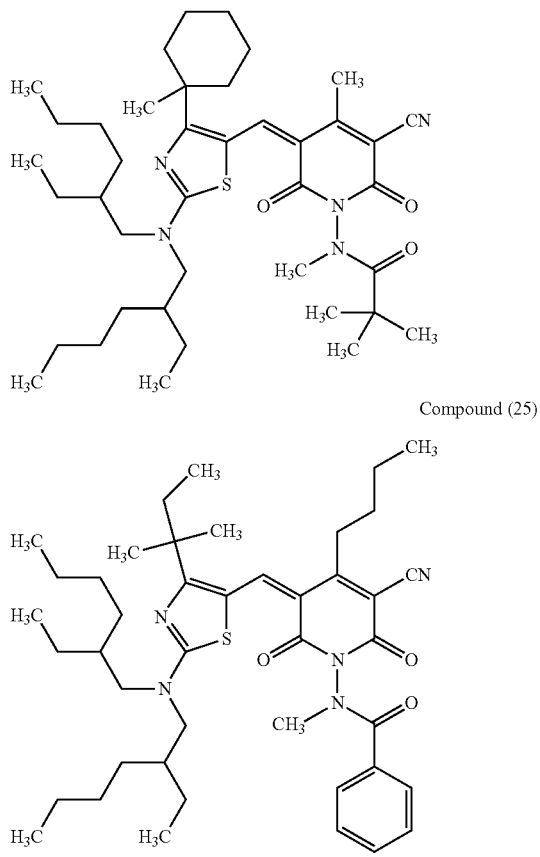

Compound (24)

Compound (25)

<Ink>

The ink of the present invention will now be described.

The coloring matter compound represented by the general formula (1) of the present invention is excellent in the light resistance and is properly applied also to a coloring agent for an ink.

The ink of the present invention is an ink containing the coloring matter compound represented by the general formula (1), and a medium for dissolving or dispersing the coloring matter compound. The content of the coloring matter compound in the ink of the present invention is preferably 0.1 to 200.0 parts by mass based on 1000.0 parts by mass of the medium. The content is more preferably 1.0 to 100.0 parts by mass, and further more preferably 5.0 to 80.0 parts by mass. When the content falls in this range, the dispersibility of the coloring agent can be good while attaining sufficient coloring power.

In the ink of the present invention, components other than the above can be individually determined according to the application of the ink of the present invention, and additives may be appropriately added as long as properties for various applications of the ink are not impeded.

The ink of the present invention can be suitably used not only as an inkjet ink but also as a printing ink, a coating material or an ink for a writing tool. In particular, the ink of the present invention can be suitably used as an ink for a resist for a color filter or for a heat-sensitive transfer recording sheet described later.

The ink of the present invention is obtained as follows:

The coloring matter compound of the present invention is gradually added to a medium with stirring, if necessary, together with another coloring agent, an emulsifier or a resin, so as to be sufficiently mixed with the medium. Furthermore, the compound is stably dissolved or dispersed by applying mechanical shearing force with a disperser, and thus, an ink of the present invention can be obtained.

The "medium" herein means water or an organic solvent.

If an organic solvent is used as the medium of the ink of the present invention, the type of the organic solvent is not especially limited but may be determined according to the application of the coloring agent. Specific examples include: alcohols such as methanol, ethanol, denatured ethanol, isopropanol, n-butanol, isobutanol, tert-butanol, sec-butanol, 2-methyl-2-butanol, 3-pentanol, octanol, benzyl alcohol, and cyclohexanol; glycols such as methyl cellosolve, ethyl cellosolve, diethylene glycol, and diethylene glycol monobutyl ether; ketones such as acetone, methyl ethyl ketone, and methyl isobutyl ketone; esters such as ethyl acetate, butyl acetate, ethyl propionate, and cellosolve acetate; aliphatic hydrocarbons such as hexane, octane, petroleum ether, and cyclohexane; aromatic hydrocarbons such as benzene, toluene, and xylene; halogenated hydrocarbons such as carbon tetrachloride, trichloroethylene, and tetrabromoethane; ethers such as diethyl ether, dimethyl glycol, trioxane, and tetrahydrofuran; acetals such as methylal and diethyl acetal; organic acids such as formic acid, acetic acid and propionic acid; and sulfur- or nitrogen-containing organic compounds such as nitrobenzene, dimethyl amine, monoethanol amine, pyridine, dimethyl sulfoxide, and dimethylformamide.

Furthermore, as the organic solvent usable in the ink of the present invention, a polymerizable monomer can be used. The polymerizable monomer is an addition polymerizable monomer or a condensation polymerizable monomer, and can be an addition polymerizable monomer. Examples of such polymerizable monomers include: styrene monomers such as styrene, α-methylstyrene, α-ethylstyrene, o-methylstyrene, m-methylstyrene, p-methylstyrene, o-ethylstyrene, m-ethylstyrene and p-ethylstyrene; acrylate monomers such as methyl acrylate, ethyl acrylate, propyl acrylate, butyl acrylate, octyl acrylate, dodecyl acrylate, stearyl acrylate, behenyl acrylate, 2-ethylhexyl acrylate, dimethylaminoethyl acrylate, diethylaminoethyl acrylate, acrylonitrile and acrylic acid amide; methacrylate monomers such as methyl methacrylate, ethyl methacrylate, propyl methacrylate, butyl methacrylate, octyl methacrylate, dodecyl methacrylate, stearyl methacrylate, behenyl methacrylate, 2-ethylhexyl methacrylate, dimethylaminoethyl methacrylate, diethylaminoethyl methacrylate, methacrylonitrile and methacrylic acid amide; olefin monomers such as ethylene, propylene, butylene, butadiene, isoprene, isobutylene and cyclohexene; halogenated vinyl monomers such as vinyl chloride, vinylidene chloride, vinyl bromide and vinyl iodide; vinyl ester monomers such as vinyl acetate, vinyl propionate and vinyl benzoate; vinyl ether monomers such as vinyl methyl ether, vinyl ethyl ether and vinyl isobutyl ether; and vinyl ketone monomers such as vinyl methyl ketone, vinyl hexyl ketone and methyl isopropenyl ketone. One of these can be singly used, or two or more of these can be used in combination.

The coloring matter compound represented by the general formula (1) is used as the coloring agent contained in the ink of the present invention, and a second coloring agent may be used together as occasion demands as long as the solubility or dispersibility of the coloring matter compound in the medium is not impeded.

Examples of the second coloring agent usable together include, but are not limited to, a condensed azo compound, an azo metal complex, a diketopyrrolopyrrole compound, an anthraquinone compound, a quinacridone compound, a naphthol compound, a benzimidazolone compound, a thioindigo compound, a perylene compound, a methine compound, an allylamide compound, and a basic dye lake compound. Specific examples include C.I. Pigment Orange 1, 5, 13, 15, 1.6, 34, 36, 38, 62, 64, 67, 72 and 74; C.I. Pigment Red 2, 3, 4, 5, 6, 7, 12, 16, 17, 23, 31, 32, 41, 48, 48:1, 48:2, 48:3, 48:4, 53:1, 57:1, 81:1, 112, 122, 123, 130, 144, 146, 149, 150, 166, 168, 169, 170, 176, 177, 178, 179, 181, 184, 185, 187, 190, 194, 202, 206, 208, 209, 210, 220, 221, 224, 238, 242, 245, 253, 254, 255, 258, 266, 269 and 282; C.I. Pigment Violet 13, 19, 25, 32 and 50; and various coloring agents and the like classified as derivatives of these.

The content of the coloring agent in the ink of the present invention is preferably 1.0 to 30.0 parts by mass based on 100.0 parts by mass of the medium.

If water is used as the medium of the ink of the present invention, an emulsifier may be added if necessary for attaining good dispersion stability of the coloring agent. The emulsifier that can be added is not especially limited, and examples include a cationic surfactant, an anionic surfactant and a nonionic surfactant.

Examples of the cationic surfactant include dodecyl ammonium chloride, dodecyl ammonium bromide, dodecyl trimethyl ammonium bromide, dodecyl pyridinium chloride, dodecyl pyridinium bromide, and hexadecyl trimethyl ammonium bromide.

Examples of the anionic surfactant include fatty acid soap such as sodium stearate and sodium dodecanoate; sodium dodecyl sulfate, sodium dodecylbenzene sulfate, and sodium lauryl sulfate.

Examples of the nonionic surfactant include dodecyl polyoxyethylene ether, hexadecyl polyoxyethylene ether, nonylphenyl polyoxyethylene ether, lauryl polyoxyethylene ether, sorbitan monoleate polyoxyethylene ether, and monodecanoyl sucrose.

The ink of the present invention may further contain a resin. The type of resin that may be contained in the ink of the present invention is not especially limited but can be determined according to the application, and examples include a polystyrene resin, a styrene copolymer, a polyacrylic acid resin, a polymethacrylic acid resin, a polyacrylate resin, a polymethacrylate resin, an acrylic acid copolymer, a methacrylic acid copolymer, a polyester resin, a polyvinyl ether resin, a polyvinyl methyl ether resin, a polyvinyl alcohol resin, a polyvinyl butyral resin, a polyurethane resin and a polypeptide resin. One of these resins may be singly used, or two or more of these resins may be used in combination if necessary.

The disperser is not especially limited, and a media type disperser such as a rotary shearing homogenizer, a ball mill, a sand mill or an attritor, or a high-pressure counter collision disperser can be used.

As described so far, the ink of the present invention contains the coloring matter compound of the present invention, and therefore, an ink excellent in the light resistance can be provided.

<Resist Composition for Color Filter>

Next, the resist composition for a color filter of the present invention will be described.

Since the coloring matter compound of the present invention is excellent in the light resistance, the coloring matter compound can be suitably used for a resist composition for a color filter.

The resist composition for a color filter of the present invention contains a binder resin, a medium and the coloring matter compound of the present invention.

The resist composition for a color filter of the present invention is obtained as follows: The coloring matter compound and a binder resin are added to a medium with stirring. At this point, a polymerizable monomer, a polymerization initiator and a photoacid generator may be added if necessary. Thereafter, the aforementioned materials are stably dissolved or dispersed in the medium by applying mechanical shearing force with a disperser, and thus, the resist composition for a color filter of the present invention can be obtained.

In the present invention, the content of the coloring matter compound is 1 to 90% by mass and preferably 5 to 70% by mass and the content of the binder resin is 5 to 90% by mass and preferably 10 to 70% by mass based on the total amount (total solids) of the resist composition for a color filter.

The binder resin usable in the resist composition for a color filter of the present invention can be such a resin that at least either an exposed portion or a shielded portion thereof obtained in an exposure step for forming picture elements can be dissolved in an organic solvent, an alkaline aqueous solution, water or a commercially available developer. In particular, from the viewpoint of workability and a treatment performed after producing a resist, a resin having a composition that can be developed with water or an alkaline aqueous solution can be suitably used.

The binder resin can be one obtained by copolymerizing, by a known method, a hydrophilic polymerizable monomer, such as acrylic acid, methacrylic acid, N-(2-hydroxyethyl) acrylamide, N-vinyl pyrrolidone, or a polymerizable monomer having an ammonium salt, and a lipophilic polymerizable monomer, such as acrylic ester, methacrylic ester, vinyl acetate, styrene, or N-vinylcarbazole, in an appropriate mixing ratio. Such a binder resin is used in combination with a radical polymerizable monomer having an ethylenically unsaturated group, a cationic polymerizable monomer having an oxirane ring or an oxetane ring, a radical generator, an acid generator, or a base generator. This type of binder resin can be used as a negative resist in which a shielded portion alone is removed by development because the solubility of materials in a developer is lowered in an exposed portion when exposed.

Alternatively, a resin having a quinonediazide group that cleaves by light to generate a carboxylic acid group, or a combination of a binder resin having a group that cleaves by an acid such as carbonic acid tert-butyl ester of polyhydroxystyrene and tetrahydropyranyl ether with an acid generator that generates an acid by exposure can be used. This type of resin can be used as a positive resist in which an exposed portion alone is removed by development because the solubility of materials in a developer is increased in an exposed portion when exposed.

If the resist composition for a color filter of the present invention is the negative resist composition, a polymerizable monomer that is addition polymerized by exposure (hereinafter also referred to as the photopolymerizable monomer) can be used. The photopolymerizable monomer can be a compound having, in a molecule, at least one or more addition polymerizable ethylenically unsaturated double bonds and having a boiling point of 100° C. or more under normal pressure. Specific examples include polyfunctional acrylates and polyfunctional methacrylates obtained by adding ethylene oxide or propylene oxide to a monofunctional acrylate, a polyfunctional acrylate or methacrylate, or a polyfunctional alcohol, and by acrylating or methacrylating the resultant. Examples of the monofunctional acrylate include polyethylene glycol monoacrylate, polyethylene glycol monomethacrylate, polypropylene glycol monoacrylate, polypropylene glycol monomethacrylate, phenoxyethyl acrylate, and phenoxyethyl methacrylate. Examples of the polyfunctional acrylate or methacrylate include polyethylene glycol diacrylate, polyethylene glycol dimethacrylate, polypropylene glycol diacrylate, polypropylene glycol dimethacrylate, trimethylolethane triacrylate, trimethylolethane trimethacrylate, trimethylolpropane triacrylate, trimethylolpropane trimethacrylate, trimethylolpropane diacrylate, trimethylolpropane dimethacrylate, neopentyl glycol diacrylate, neopentyl glycol dimethacrylate, pentaerythritol tetraacrylate, pentaerythritol tetramethacrylate, pentaerythritol triacrylate, pentaerythritol trimethacrylate, dipentaerythritol hexaacrylate, dipentaerythritol hexamethacrylate, dipentaerythritol pentaacrylate, dipentaerythritol pentamethacrylate, hexanediol diacrylate, hexanediol dimethacrylate, trimethylolpropane tri(acryloyloxypropyl) ether, tri(acryloyloxyethyl) isocyanurate, tri(acryloyloxyethyl) cyanurate, glycerin triacrylate, and glycerin trimethacrylate. Examples of the polyfunctional alcohol include trimethylolpropane and glycerin. Other examples of the photopolymerizable monomer include urethane acrylates, polyester acrylates, and polyfunctional epoxy acrylates and epoxy methacrylates obtained as reaction products of an epoxy resin and an acrylic acid or methacrylic acid. Among the aforementioned monomers, trimethylolpropane triacrylate, trimethylolpropane trimethacrylate, pentaerythritol tetraacrylate, pentaerythritol tetramethacrylate, dipentaerythritol hexaacrylate, dipentaerythritol hexamethacrylate, dipentaerythritol pentaacrylate and dipentaerythritol pentamethacrylate can be particularly suitably used.

One of these photopolymerizable monomers may be singly used, or two or more of these may be used in combination if necessary.

The content of the photopolymerizable monomer is preferably 5 to 50% by mass and more preferably 10 to 40% by mass based on the mass (total solids) of the resist composition for a color filter of the present invention. If the content is 5 to 50% by mass, sensitivity to the exposure and the strength of picture elements can be further improved, and in addition, the viscosity of the resist composition for a color filter can be placed in an appropriate state.

If the resist composition for a color filter of the present invention is the negative resist composition, a photopolymerization initiator may be added. Examples of the photopolymerization initiator include a vicinalpolyketoaldonyl compound, an α-carbonyl compound, acyloin ether, a multibranch quinone compound, a combination of a triallylimidazole dimer and p-aminophenylketone, and a trioxadiazole compound. In particular, 2-benzyl-2-dimethylamino-1-(4-morpholinophenyi) butanone (trade name: IRGACURE 369, manufactured by BASF) can be suitably used. Incidentally, if electron beams are used for forming picture elements by using the resist composition for a color filter of the present invention, it is not always necessary to use the photopolymerization initiator.

If the resist composition for a color filter of the present invention is the positive resist composition, a photoacid generator may be added as occasion demands. As the photoacid generator, known photoacid generators such as a salt of onium ions of sulfonium, iodonium, selenium, ammonium or phosphonium, and anions can be used.

Examples of the sulfonium ions include those of triphenylsulfonium, tri-p-tolylsulfonium, tri-o-tolylsulfonium, tris(4-methoxyphenyl)sulfonium, 1-naphthyldiphenylsulfonium, diphenylphenacylsulfonium, phenylmethylbenzylsulfonium, 4-hydroxyphenylmethylbenzylsulfonium, dimethylphenacylsulfonium, and phenacyltetrahydrothiophenium.

Examples of the iodonium ions include those of diphenyliodonium, di-p-tolyliodonium, bis(4-dodecylphenyl)iodonium, bis(4-methoxyphenyl)iodonium, and (4-octyloxyphenyl)phenyliodonium.

Examples of the selenium ions include those of triarylselenium such as triphenylselenium, tri-p-tolylselenium, tri-o-tolylselenium, tris(4-methoxyphenyl)selenium, 1-naphthyldiphenylselenium, tris(4-fluorophenyl)selenium, tri-1-naphtylselenium, and tri-2-naphthylselenium.

Examples of the ammonium ions include those of tetraalkylammonium such as tetramethylammonium, ethyl trimethylammonium, diethyldimethylammonium, triethylmethylammonium, tetraethylammonium, trimethyl-n-propylammonium, trimethylisopropylammonium, trimethyl-n-butylammonium, and trimethylisobutylammonium.

Examples of the phosphonium ions include those of tetraphenylphosphsphonium, tetra-p-tolylphosphonium, tetrakis(2-methoxyphenyl)phosphonium, triphenylbenzylphosphonium, triphenylphenacylphosphonium, triphenylmethylphosphonium, triethylbenzyphosphonium, and tetraethylphosphonium.

Examples of the anions include, but are not limited to, halogen acid ions such as $ClO_4^-$ and $BrO_4^-$, halogenated sulfonic acid ions such as $FSO_3^-$ and $ClSO_3^-$, sulfuric acid ions such as $CH_3SO_4^-$, $CF_3SO_4^-$ and $HSO_4^-$, carbonic acid ions such as $HCO_3^-$ and $CH_3CO_3^-$, aluminic acid ions such as $AlCl_4^-$ and $AlF_4^-$, hexafluorobismuthic acid ions, carboxylic acid ions such as $CH_3COO^-$, $CF_3COO^-$, $C_6H_5COO^-$, $CH_3C_6H_4COO^-$, $C_6F_5COO^-$, and $CF_3C_6H_4COO^-$, aryiboric acid ions such as $B(C_6H_5)_4^-$ and $CH_3CH_2CH_2CH_2B(C_6H_5)_3^-$, thiocyanic acid ions, and nitric acid ions.

In the resist composition for a color filter of the present invention, the medium used for dissolving or dispersing the coloring matter compound, the binder resin, and the photopolymerizable monomer, the photopolymerization initiator and the photoacid generator added as occasion demands, can be water or an organic solvent. Examples of the organic solvent include cyclohexanone, ethyl cellosolve acetate, butyl cellosolve acetate, 1-methoxy-2-propyl acetate, diethylene glycol dimethyl ether, ethyl benzene, 1,2,4-trichlorobenzene, ethylene glycol diethyl ether, xylene, ethyl cellosolve, methyl-n-amyl ketone, propylene glycol monomethyl ether, toluene, methyl ethyl ketone, ethyl acetate, methanol, ethanol, isopropanol, butanol, methyl isobutyl ketone, and a petroleum solvent. One of these solvents may be singly used, or two or more of these may be used in combination. Furthermore, the medium of the resist composition for a color filter of the present invention may be the same as the medium used in preparing the ink as long as the dispersibility of the coloring matter compound is not impeded.

In a color filter in which two or more types of picture elements having different spectral properties are adjacently arranged, the resist composition for a color filter of the present invention is used for picture elements of at least one color out of the plurality of colors (such as red, green and blue) of the picture elements, and thus, a color filter having excellent light resistance can be obtained. Furthermore, in order to attain desired spectral properties, another coloring agent may be used together for purpose of color matching. A coloring agent that can be used together is not especially limited, and examples include a condensed azo compound, an azo metal complex, a diketopyrrolopyrrole compound, an anthraquinone compound, a quinacridone compound, a naphthol compound, a benzimidazolone compound, a thioindigo compound, a perylene compound, a methine compound, an allylamide compound, and a basic dye lake compound. Specific examples include C.I. Pigment Orange 1, 5, 13, 15, 16, 34, 36, 38, 62, 64, 67, 72 and 74; C.I. Pigment Red 2, 3, 4, 5, 6, 7, 12, 16, 17, 23, 31, 32, 41, 48, 48:1, 48:2, 48:3, 48:4, 53:1, 57:1, 81:1, 112, 122, 123, 130, 144, 146, 149, 150, 166, 168, 169, 170, 176, 177, 178, 179, 181, 184, 185, 187, 190, 194, 202, 206, 208, 209, 210, 220, 221, 224, 238, 242, 245, 253, 254, 255, 258, 266, 269 and 282; C.I. Pigment Violet 13, 19, 25, 32 and 50; and various coloring agents and the like classified as derivatives of these.

The resist composition for a color filter of the present invention may contain, apart from the aforementioned additives, an ultraviolet absorber, or a silane coupling agent used for improving adhesion to a glass substrate in producing a filter, as occasion demands.

The disperser to be used is not especially limited, and a media type disperser such as a rotary shearing homogenizer, a ball mill, a sand mill or an attritor, or a high-pressure counter collision disperser can be used.

As described so far, the resist composition for a color filter of the present invention contains the coloring matter compound of the present invention, and therefore, a resist compound for a color filter excellent in light resistance can be provided.

<Heat-Sensitive Transfer Recording Sheet>

Next, the heat-sensitive transfer recording sheet of the present invention will be described.

The coloring matter compound of the present invention is excellent in light resistance, and thus can be suitably used for a heat-sensitive transfer recording sheet.

The heat-sensitive transfer recording sheet of the present invention is characterized by including: a substrate; and a coloring material layer containing the coloring matter compound of the present invention.

The heat-sensitive transfer recording sheet of the present invention is obtained as follows: A coloring agent containing a coloring matter compound represented by the general formula (1), a binder resin, and a surfactant and a wax if necessary, are gradually added to a medium with stirring, so as to be sufficiently mixed with the medium. Furthermore, the components are stably dissolved or finely dispersed by applying mechanical shearing force with a disperser, and thus, an ink of the present invention is prepared. Next, the ink is applied on a base film used as a substrate and then dried, and thus, a heat-sensitive transfer recording sheet of the present invention can be prepared. Incidentally, the heat-sensitive transfer recording sheet of the present invention may contain the coloring matter compound represented by the general formula (1), and hence, the heat-sensitive transfer recording sheet of the present invention is not limited to one obtained by this preparation method.

Various resins may be used as the binder resin for the heat-sensitive transfer recording sheet of the present invention. In particular, water soluble resins such as a cellulose resin, a polyacrylic acid resin, a starch resin and an epoxy resin; and organic solvent soluble resins such as a polyacrylate resin, a polymethacrylate resin, a polystyrene resin, a polycarbonate resin, a polyether sulfone resin, a polyvinyl butyral resin, an ethyl cellulose resin, an acetyl cellulose resin, a polyester resin, an AS resin (styrene acrylonitrile copolymer), and a phenoxy resin can be suitably used. One of these resins may be singly used, or two or more of these may be used in combination as occasion demands.

As the medium usable in the aforementioned preparation method, those usable as the medium of the ink can be used. Specifically, water or an organic solvent can be used. As the organic solvent, alcohols such as methanol, ethanol, isopropanol, and isobutanol; cellosolves such as methyl cellosolve and ethyl cellosolve; aromatic hydrocarbons such as toluene, xylene and chlorobenzene; esters such as ethyl acetate and butyl acetate; ketones such as acetone, methyl ethyl ketone, methyl isobutyl ketone, and cyclohexanone; halogenated hydrocarbons such as methylene chloride, chloroform and trichloroethylene; ethers such as tetrahydrofuran and dioxane; and N,N-dimethylformamide and N-methyl pyrrolidone can be suitably used. One of these organic solvents may be singly used, or two or more of these may be used in combination if necessary.

In the heat-sensitive transfer recording sheet of the present invention, the coloring matter compound represented by the general formula (1) is used as a coloring agent, and therefore, a heat-sensitive transfer recording sheet excellent in light resistance can be obtained. Furthermore, a second coloring agent may be used together for purpose of color matching, so as to attain desired spectral properties. The coloring agent that can be used together is not especially limited as long as the brightness, the saturation and the light resistance of the heat-sensitive transfer recording sheet of the present invention are not largely affected, and examples include a condensed azo compound, an azo metal complex, a diketopyrrolopyrrole compound, an anthraquinone compound, a quinacridone compound, a naphthol compound, a benzimidazolone compound, a thioindigo compound, a perylene compound, a methine compound, an allylamide compound, and a basic dye lake compound. Specific examples include: C.I. Pigment Orange 1, 5, 13, 15, 16, 34, 36, 38, 62, 64, 67, 72, 74; C.I. Pigment Red 2, 3, 4, 5, 6, 7, 12, 16, 17, 23, 31, 32, 41, 48, 48:1, 48:2, 48:3, 48:4, 53:1, 57:1, 81:1, 112, 122, 123, 130, 144, 146, 149, 150, 166, 168, 169, 170, 176, 177, 178, 179, 181, 184, 185, 187, 190, 194, 202, 206, 208, 209, 210, 220, 221, 224, 238, 242, 245, 253, 254, 255, 258, 266, 269, 282; C.I. Pigment Violet 13, 19, 25, 32, 50, and various coloring agents classified as derivatives of these.

The ratio of the used binder resin to coloring agent (binder resin: coloring agent) can be 1:2 to 2:1 in a mass ratio from the viewpoint of transferability.

The heat-sensitive transfer recording sheet of the present invention may contain a surfactant so as to attain sufficient lubricity at the time when heated with a thermal head (at the time of printing). Examples of the surfactant that can be contained include a cationic surfactant, an anionic surfactant and a nonionic surfactant.

Examples of the cationic surfactant include dodecyl ammonium chloride, dodecyl ammonium bromide, dodecyl trimethyl ammonium bromide, dodecyl pyridinium chloride, dodecyl pyridinium bromide, and hexadecyl trimethyl ammonium bromide.

Examples of the anionic surfactant include fatty acid soap such as sodium stearate and sodium dodecanoate; sodium dodecyl sulfate, sodium dodecylbenzene sulfate, and sodium lauryl sulfate.

Examples of the nonionic surfactant include dodecyl polyoxyethylene ether, hexadecyl polyoxyethylene ether, nonylphenyl polyoxyethylene ether, lauryl polyoxyethylene ether, sorbitan monooleate polyoxyethylene ether, and monodecanoyl sucrose.

The heat-sensitive transfer recording sheet of the present invention may contain a wax so as to attain sufficient lubricity at the time when not heated with the thermal heat. Examples of the wax that may be contained include, but are not limited to, a polyethylene wax, a paraffin wax and a fatty acid ester wax.

The heat-sensitive transfer recording sheet of the present invention may contain, if necessary, an ultraviolet absorber, an antiseptic agent, an antioxidant, an antistatic agent, and a viscosity modifier in addition to the aforementioned additives.

The base film used as the substrate of the heat-sensitive transfer recording sheet of the present invention is not especially limited, and condenser paper, thin paper such as glassine paper, and films of plastics such as polyester, polycarbonate, polyamide, polyimide and aramide are preferably used from the viewpoint of good heat resistance, and a polyethylene terephthalate film is more preferably used from the viewpoint of mechanical strength, solvent resistance and economic efficiency. The thickness of the substrate can be 3 to 50 μm from the viewpoint of the transferability.

The heat-sensitive transfer recording sheet of the present invention can be provided, on a face of the substrate opposite to the face having the coloring material layer, with a layer of a lubricant, heat-resistant fine particles with high lubricity, and a thermal resin such as a binding agent, for purposes of improving the heat resistance and the travelling performance of the thermal head. Examples of the lubricant include an amino-modified silicone compound and a carboxyl-modified silicone compound. Examples of the heat-resistant fine particles include fine particles such as silica, and an example of the binding agent includes an acrylic resin, but these examples do not limit these substances.

The disperser used in the dispersion step is not especially limited, and a media type disperser such as a rotary shearing homogenizer, a ball mill, a sand mill or an attritor, or a high-pressure counter collision disperser can be used.

A method for applying the ink on the base film is not especially limited, and methods using a bar coater, a gravure coater, a reverse roll coater, a rod coater, and an air doctor coater can be employed. With respect to the amount of ink to be applied, the composition can be applied so as to attain a thickness of the coloring material layer after drying in the range of 0.1 to 5 μm from the viewpoint of the transferability.

Methods for heating the heat-sensitive transfer recording sheet of the present invention are not especially limited, and not only a general method using a thermal head but also a method using infrared rays or laser beams can be employed. Alternatively, the heat-sensitive transfer recording sheet of the present invention may be used as an electrical dye transfer sheet by using, as the base film itself, an electrically exothermic film that generates heat when electricity flows therein.

As described so far, the heat-sensitive transfer recording sheet of the present invention can be provided as a heat-sensitive transfer recording sheet excellent in light resistance.

EXAMPLES

The present invention will now be described in more detail with reference to examples and comparative examples, and it is noted that the present invention is not limited to these examples. In the following description, the terms "part(s)" and "%" are used on a mass basis unless otherwise mentioned. Obtained compounds were identified by using a $^1$H nuclear magnetic resonance ($^1$H-NMR) spectrometer (ECA-400, manufactured by JEOL Ltd.) and an LC/TOF MS (LC/MSD TOF, manufactured by Agilent Technologies Inc.).

Preparation of Coloring Matter Compound Represented by the General Formula (1)

A coloring matter compound represented by the general formula (1) of the present invention can be synthesized by known methods.

Coloring matter compounds represented by the general formula (1) of the present invention were prepared as follows:

Preparation Example 1

Preparation of Compound (1)

To a 20 mL toluene suspension of 10 mmol of the pyridone compound (1), 100 mg of p-toluenesulfonic acid was added, the resulting solution was heated to 70° C., and a 20 mL toluene solution of 10 mmol of the aldehyde compound (1) was added dropwise thereto. The resultant was refluxed by heating at 160° C. for 6 hours while performing azeotropic dehydration. After completing the reaction, the resulting solution was cooled to room temperature, and diluted with isopropanol. After the diluted solution was concentrated under reduced pressure, the thus obtained residue was purified by column chromatography (eluent: ethyl acetate/heptane), so as to give 4.6 g (yield: 78%) of a compound (1). FIGURE illustrates a $^1$H-NMR spectrum of the compound (1) obtained in CDCl$_3$ at room temperature at 400 MHz.

Analysis Result of Compound (1)

[1] $^1$H-NMR (400 MHz, CDCl$_3$, room temperature): δ (ppm)=0.97 (3H, t, J=7.33 Hz), 1.03 (3H, t, J=7.33 Hz), 1.36 (2H, dd, J=7.33, 14.7 Hz), 1.43-1.58 (11H, m), 1.66-1.78 (4H, m), 2.48 (3H, s), 2.56 (3H, s), 3.50 (2H, t, J=7.56 Hz), 3.80 (2H, t, J=7.33 Hz), 7.34 (2H, t, J=7.56 Hz), 7.45 (1H, t, J=6.87 Hz), 7.68 (2H, d, J=8.24 Hz), 8.24 (1H, s)

[2] Mass Spectrometry (ESI-TOF): m/z=590.2989 (M+H)$^+$

Preparation Example 2

Preparation of Compound (3)

A 50 mL methanol solution of 10 mmol of the aldehyde compound (2) and 10 mmol of the pyridone compound (4) was stirred at room temperature for 3 days. After completing the reaction, the resulting solution was diluted with isopropanol and filtered, so as to give 5.4 g (yield: 82%) of a compound (3).

Analysis Result of Compound (3)

[1] $^1$H-NMR (400 MHz, CDCl$_3$, room temperature): δ (ppm)=0.93 (12H, q, J=6.87 Hz), 1.14 (6H, s), 1.30-1.39 (17H, m), 1.39-1.60 (11H, m), 1.84-1.92 (2H, m), 2.54 (3H, s), 3.16 (2H, s), 3.37-3.48 (3H, m), 3.58-3.92 (2H, dm), 8.31 (1H, s)

[2] Mass Spectrometry (ESI-TOF): m/z=654.4611 (M+H)$^+$

Preparation Example 3

Preparation of Compound (6)

A 50 mL ethanol solution of 10 mmol of the aldehyde compound (2) and 10 mmol of the pyridone compound (7) was stirred at room temperature for 3 days. After completing the reaction, the resulting solution was diluted with isopropanol and filtered, so as to give 5.1 g (yield: 87%) of a compound (6).

Analysis Result of Compound (6)

[1] $^1$H-NMR (400 MHz, CDCl$_3$, room temperature): δ (ppm)=0.92 (12H, q, J=7.02 Hz), 1.22-1.41 (16H, m), 1.54 (9H, s), 1.85-1.90 (2H, m), 2.50 (3H, s), 3.00 (6H, s), 3.37 (2H, d, J=5.50 Hz), 3.73 (2H, dq, J=4.27, 17.2 Hz), 8.28 (1H, s)

[2] Mass Spectrometry (ESI-TOF): m/z=584.4211 (M+H)$^+$

Preparation Example 4

Preparation of Compound (10)

In the same manner as in Preparation Example 2 except that the pyridone compound (9) was used instead of the pyridone compound (4), 4.8 g (yield: 77%) of a compound (10) was obtained.

Analysis Result of Compound (10)

[1] $^1$H-NMR (400 MHz, CDCl$_3$, room temperature): δ (ppm)=0.92 (12H, dt, J=7.90, 23.1 Hz), 1.20-1.34 (18H, m), 1.53 (3H, s), 1.73 (4H, q, J=5.65 Hz), 1.86-1.93 (2H, m), 2.49 (3H, s), 3.22 (2H, dd, J=4.58, 10.1 Hz), 3.37-3.41 (4H, min), 3.71-3.75 (2H, m), 8.24 (1H, s)

[2] Mass Spectrometry (ESI-TOF): m/z=624.4531 (M+H)$^+$

Preparation Examples 5 to 12

Preparation of Compounds (4), (12), (13), (15), (18), (20), (21) and (22)

Corresponding compounds (4), (12), (13), (15), (18), (20), (21) and (22) were obtained in the same manner as in Preparation Example 2 except that the aldehyde compound (2) and the pyridone compound (4) were respectively changed to corresponding aldehyde compounds and pyridone compounds.

Analysis Result of Compound (4)

[1] $^1$H-NMR (400 MHz, CDCl$_3$, room temperature): δ (ppm)=0.90-1.01 (15H, m), 1.14 (7H, s), 1.24-1.39 (16H, m), 1.52-1.66 (13H, m), 1.82-1.92 (2H, m), 2.84-2.89 (2H, m), 3.16 (2H, s), 3.37-3.42 (3H, m), 3.61-3.94 (2H, m), 8.29 (1H, d, J=9.62 Hz)

[2] Mass Spectrometry (ESI-TOF): m/z=696.4972 (M+H)$^+$

Analysis Result of Compound (12)

[1] $^1$H-NMR (400 MHz, CDCl$_3$, room temperature): δ (ppm)=0.98 (6H, q, J=7.33 Hz), 1.14 (7H, s), 1.33-1.44 (6H, m), 1.56 (9H, t, J=14.2 Hz), 1.64-1.75 (4H, m), 2.54 (3H, d, J=13.3 Hz), 3.17 (2H, s), 3.48 (3H, t, J=8.01 Hz), 3.80 (2H, t, J=7.33 Hz), 8.31 (1H, s)

[2] Mass Spectrometry (ESI-TOF): m/z=542.3279 (M+H)$^+$

Analysis Result of Compound (13)

[1] $^1$H-NMR (400 MHz, CDCl$_3$, room temperature): δ (ppm)=0.94 (12H, tt, J=5.88, 18.3 Hz), 1.27-1.46 (16H, m), 1.55 (9H, s), 1.87-1.95 (2H, m), 2.43 (3H, s), 3.29-3.44 (5H, m), 3.60-3.92 (2H, m), 7.21-7.33 (3H, m), 7.44-7.49 (2H, m), 8.17 (1H, s)

[2] Mass Spectrometry (ESI-TOF): m/z=674.4189 (M+H)$^+$

Analysis Result of Compound (15)

[1] $^1$H-NMR (400 MHz, CDCl$_3$, room temperature): δ (ppm)=0.89-0.96 (15H, m), 1.22-1.42 (18H, m), 1.57 (8H, t, J=16.5 Hz), 1.88-1.91 (9H, m), 2.01-2.13 (4H, m), 2.57 (3H, s), 3.12 (3H, s), 3.38-3.57 (2H, d, J=13.3 Hz), 3.73-3.96 (2H, m), 8.33 (1H, s)

[2] Mass Spectrometry (ESI-TOF): m/z=732.4933 (M+H)$^+$

Analysis Result of Compound (18)

[1] $^1$H-NMR (400 MHz, CDCl$_3$, room temperature): δ (ppm)=0.87-0.95 (12H, m), 1.11-1.24 (8H, m), 1.30-1.38 (18H, m), 1.53-1.60 (12H, t, J=13.5 Hz), 1.84-1.92 (1H, m), 2.54 (3H, d, J=11.5 Hz), 3.37-3.41 (2H, m), 3.54-3.91 (4H, m), 8.31 (1H, d, J=11.9 Hz)

[2] Mass Spectrometry (ESI-TOF): m/z=668.4662 (M+H)$^+$

Analysis Result of Compound (20)

[1] $^1$H-NMR (400 MHz, CDCl$_3$, room temperature): δ (ppm)=0.89-1.01 (15H, m), 1.25-1.42 (16H, m), 1.56 (11H, t, J=10.5 Hz), 1.60-1.75 (2H, m), 1.82-1.95 (5H, m), 2.86-2.91 (2H, m), 3.19 (3H, m), 3.35-3.42 (2H, m), 3.73-3.79 (2H, m), 8.32 (1H, s)

[2] Mass Spectrometry (EST-TOF): m/z=654.4399 (M+H)$^+$

Analysis Result of Compound (21)

[1] $^1$H-NMR (400 MHz, CDCl$_3$, room temperature): δ (ppm)=0.88-1.01 (17H, m), 1.24-1.46 (18H, m), 1.51 (9H, s), 1.87-1.96 (2H, m), 2.70-2.74 (2H, m), 3.33 (3H, s), 3.40-3.50 (2H, m), 3.61-3.86 (2H, m), 7.22 (2H, t, J=7.56 Hz), 7.46 (3H, t, J=8.70 Hz), 8.15 (1H, s)

[2] Mass Spectrometry (ESI-TOF): m/z=716.4511 (M+H)$^+$

Analysis Result of Compound (22)

[1] $^1$H-NMR (400 MHz, CDCl$_3$, room temperature): δ (ppm)=0.81 (2H, t, J=6.18 Hz), 0.89-0.95 (12H, m), 1.03 (8H, t, J=3.66 Hz), 1.14 (7H, d, J=1.83 Hz), 1.26-1.39 (17H, m), 1.55 (12H, t, J=5.95 Hz), 1.84-1.91 (3H, m), 2.69-2.81 (1H, m), 2.98-3.08 (1H, m), 3.18 (2H, J=1.83 Hz), 3.45-3.48 (3H, m), 3.56-3.89 (2H, m), 8.32 (1H, t, J=6.87 Hz)

[2] Mass Spectrometry (ESI-TOF): m/z=738.5329 (M+H)$^+$

<Production of Ink>

Inks of the present invention and comparative inks were produced as follows:

Production Example of Ink (1)

Five parts of the compound (1), that is, a coloring matter compound of the present invention, 350 parts of toluene, 350 parts of ethyl acetate and 300 parts of 2-butanone were mixed to produce an ink (1) of the present invention.

Production Examples of Inks (2) to (12)

Inks (2) to (12) were obtained in the same manner as in Production Example of the ink (1) except that the compound (1) was changed to used compounds shown in Table 1.

Production Examples of Comparative Inks (1) to (3)

Comparative inks (1) to (3) were obtained in the same manner as in Production Example of the ink (1) except that the compound (1) was changed to the following comparative compounds (1) to (3):

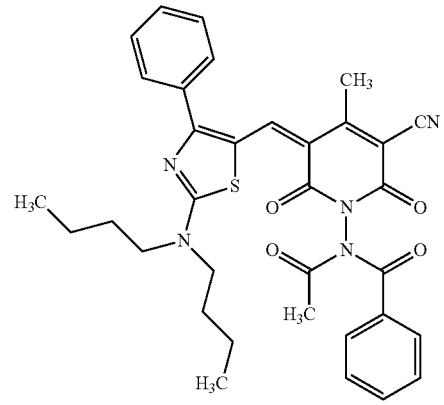

Comparative compound (1)

-continued

Comparative compound (2)

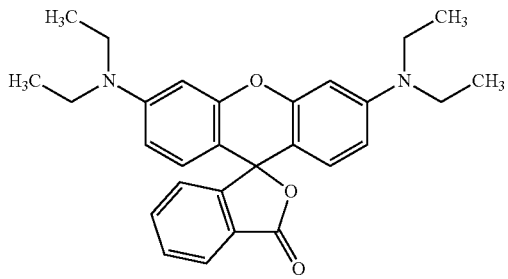

Comparative compound (3)

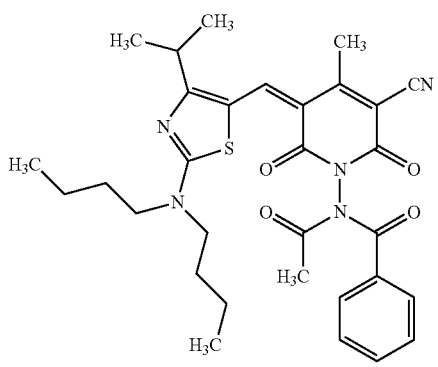

<Evaluation>

<Preparation of Samples>

Image samples were prepared by applying, by a bar coating method (with a bar No. 10), the inks (1) to (12) and the comparative inks (1) to (3) on hiding charts and air-drying the resulting charts overnight. Each of the thus prepared image samples was measured for chromaticity (L*, a* and b*) in the L*a*b* color system by using a reflection densitometer, Spectro Lino (manufactured by Gretag Macbeth AG).

Evaluation of Light Resistance of Compounds

Each image sample was loaded in a xenon weatherometer (Atlas Ci 4000, manufactured by Suga Test Instruments Co., Ltd.), and was exposed for 15 hrs. under conditions of illumination of 0.39 W/m² at 340 nm, a temperature of 40° C. and relative humidity of 60%. The reflection density of the printed product was measured before and after the test. Assuming that the initial chromaticity values were $a_0^*$, $b_0^*$ and $L_0^*$, and that the chromaticity values attained after the exposure were a*, b* and L*, a color difference ΔE was defined and calculated as follows:

$$\Delta E = \sqrt{(a^* - a_0^*)^2 + (b^* - b_0^*)^2 + (L^* - L_0^*)^2}$$

Evaluation criteria are as follows:

A: ΔE<5.00 (which means that the light resistance is extremely excellent);

B: 5.00≤ΔE<10.0 (which means that the light resistance is excellent); and

C: 10.0≤ΔE (which means that the light resistance is poor).

The evaluation results of the examples and comparative examples are shown in Table 1 below.

TABLE 1

| | Ink | Used compound | ΔE attained after 15 hrs. | Evaluation of light resistance |
|---|---|---|---|---|
| Example 1 | Ink (1) | Compound (1) | 6.70 | B |
| Example 2 | Ink (2) | Compound (3) | 2.73 | A |
| Example 3 | Ink (3) | Compound (6) | 3.28 | A |
| Example 4 | Ink (4) | Compound (10) | 4.70 | A |
| Example 5 | Ink (5) | Compound (12) | 7.20 | B |
| Example 6 | Ink (6) | Compound (13) | 4.74 | A |
| Example 7 | Ink (7) | Compound (15) | 4.72 | A |
| Example 8 | Ink (8) | Compound (18) | 8.74 | B |
| Example 9 | Ink (9) | Compound (4) | 5.36 | B |
| Example 10 | Ink (10) | Compound (20) | 5.14 | B |
| Example 11 | Ink (11) | Compound (21) | 5.32 | B |
| Example 12 | Ink (12) | Compound (22) | 5.85 | B |
| Comparative Example 1 | Comparative ink (1) | Comparative compound (1) | 10.3 | C |
| Comparative Example 2 | Comparative ink (2) | Comparative compound (2) | 64.9 | C |
| Comparative Example 3 | Comparative ink (3) | Comparative compound (3) | 11.3 | C |

As is obvious from Table 1, it is understood that the coloring matter compounds represented by the general formula (1) of the present invention are better in the light resistance than the comparative compounds.

Preparation of Resist Composition for Color Filter

Example 13

Twelve parts of the compound (1), that is, a coloring matter compound of the present invention, was mixed with 120 parts of cyclohexanone, and dispersed for 1 hour by using an attritor (manufactured by Mitsui Kozan KK), so as to give an ink (1) for producing the resist composition of the present invention.

To a solution, in 96 parts of cyclohexanone, of 6.7 parts of an acrylic copolymer composition (having a weight average molecular weight Mw of 10,000) containing, in a monomer ratio, 40% by mass of n-butyl methacrylate, 30% by mass of acrylic acid and 30% by mass of hydroxyethyl methacrylate, 1.3 parts of dipentaerythritol pentaacrylate, and 0.4 part of 2-benzyl-2-dimethylamino-1-(4-morpholinophenyl)-butanone (serving as a photopolymerization initiator), 22 parts of the ink (1) for producing a resist composition was slowed added, followed by stirring at room temperature for 3 hours. The resulting solution was filtered with a 1.5 μm filter, so as to give a resist composition (1) for a color filter of the present invention.

The resist composition (1) for a color filter was spin-coated on a glass substrate, and dried at 90° C. for 3 minutes, and the resultant was wholly exposed and post-cured at 180° C., thereby producing a color filter (1).

Examples 14 to 20

Resist compositions (2) to (8) for a color filter were obtained in the same manner as in the preparation example of Example 13 except that the compound (1) was changed to compounds shown in Table 2. Thereafter, color filters (2) to (8) were obtained in the same manner as in Example 13 except that the resist compositions (2) to (8) for a color filter were used instead of the resist composition (1) for a color filter.

Comparative Examples 4 to 6

Comparative resist compositions (1) to (3) for a color filter were obtained in the same manner as in Example 13 except that the compound (1) was changed to the comparative compounds (1) to (3). Thereafter, comparative color filters (1) to (3) were obtained in the same manner as in Example 13 except that the comparative resist compositions (1) to (3) for a color filter were used instead of the resist composition (1) for a color filter.

Production of Heat-Sensitive Transfer Recording Sheet

Example 21

To a mixed solution, in 45 parts of methyl ethyl ketone and 45 parts of toluene, of 13.5 parts of the compound (1), that is, a coloring matter compound of the present invention, 5 parts of a polyvinyl butyral resin (Denka 3000-K, manufactured by Denki Kagaku Kogyo KK) was added in limited amounts with stirring, so as to give an ink (1) for producing a heat-sensitive transfer recording sheet of the present invention.

The ink (1) for producing a heat-sensitive transfer recording sheet was applied on a polyethylene terephthalate film (Lumirror, manufactured by Toray Industries, Inc.) having a thickness of 4.5 μm into a thickness of 1 μm after drying, and the resultant was dried, so as to produce a heat-sensitive transfer recording sheet (1).

Examples 22 to 28

Heat-sensitive transfer recording sheets (2) to (8) were obtained in the same manner as in the production example of Example 21 except that the compound (1) used as the coloring matter compound was changed to the compounds shown in Table 2.

Comparative Examples 7 to 9

Comparative heat-sensitive transfer recording sheets (1) to (3) were obtained in the same manner as in Example 21 except that the compound (1) was changed to the comparative compounds (1) to (3).

<Evaluation>
<Preparation of Samples>

Image samples were prepared by transferring, onto photographic printing paper, the heat-sensitive transfer recording sheets (1) to (8) and the comparative heat-sensitive transfer recording sheets (1) to (3) by using a modified machine of a printer, Selphy, manufactured by Cannon Inc.

Evaluation of Light Resistance

Each of the obtained color filters and the image samples obtained by heat-sensitive transfer was loaded in a xenon weatherometer (Atlas Ci 4000, manufactured by Suga Test Instruments Co., Ltd.), and was exposed for 15 hrs. under conditions of illumination of 0.39 W/m$^2$ at 340 nm, a temperature of 40° C. and relative humidity of 60%. The reflection density of the printed product was measured before and after the test. Assuming that the initial chromaticity values were $a_0^*$, $b_0^*$ and $L_0^*$, and that the chromaticity values attained after the exposure were $a^*$, $b^*$ and $L^*$, a color difference ΔE was defined and calculated as follows. The results are shown in Table 2 below.

$$\Delta E = \sqrt{(a^*-a_0^*)^2+(b^*-b_0^*)^2+(L^*-L_0^*)^2}$$

Evaluation criteria are as follows:

A: ΔE<5.00 (which means that the light resistance is extremely excellent);
B: 5.00≤ΔE<10.0 (which means that the light resistance is excellent); and
C: 10.0≤ΔE (which means that the light resistance is poor).

TABLE 2

| | Compound | Application | ΔE attained after 15 hrs. | Evaluation of light resistance |
|---|---|---|---|---|
| Example 13 | Compound (1) | Color filter (1) | 6.53 | B |
| Example 14 | Compound (3) | Color filter (2) | 2.84 | A |
| Example 15 | Compound (6) | Color filter (3) | 3.56 | A |
| Example 16 | Compound (10) | Color filter (4) | 4.51 | A |
| Example 17 | Compound (12) | Color filter (5) | 6.85 | B |
| Example 18 | Compound (13) | Color filter (6) | 4.43 | A |
| Example 19 | Compound (15) | Color filter (7) | 5.06 | B |
| Example 20 | Compound (18) | Color filter (8) | 8.55 | B |
| Example 21 | Compound (1) | Heat-sensitive transfer recording sheet (1) | 6.84 | B |
| Example 22 | Compound (3) | Heat-sensitive transfer recording sheet (2) | 2.77 | A |
| Example 23 | Compound (6) | Heat-sensitive transfer recording sheet (3) | 3.42 | A |
| Example 24 | Compound (10) | Heat-sensitive transfer recording sheet (4) | 2.94 | A |
| Example 25 | Compound (4) | Heat-sensitive transfer recording sheet (5) | 4.83 | A |
| Example 26 | Compound (20) | Heat-sensitive transfer recording sheet (6) | 5.32 | B |
| Example 27 | Compound (21) | Heat-sensitive transfer recording sheet (7) | 4.85 | A |
| Example 28 | Compound (22) | Heat-sensitive transfer recording sheet (8) | 5.23 | B |
| Comparative Example 4 | Comparative compound (1) | Comparative color filter (1) | 10.6 | C |
| Comparative Example 5 | Comparative compound (2) | Comparative color filter (2) | 65.7 | C |
| Comparative Example 6 | Comparative compound (3) | Comparative color filter (3) | 12.5 | C |
| Comparative Example 7 | Comparative compound (1) | Comparative heat-sensitive transfer recording sheet (1) | 11.3 | C |
| Comparative Example 8 | Comparative compound (2) | Comparative heat-sensitive transfer recording sheet (2) | 66.2 | C |
| Comparative Example 9 | Comparative compound (3) | Comparative heat-sensitive transfer recording sheet (3) | 11.8 | C |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-188149, filed Aug. 29, 2012, which is hereby incorporated by reference herein in its entirety.

What is claimed is:

1. A coloring matter compound represented by the following general formula (1):

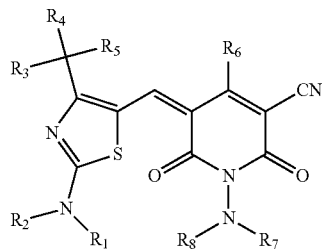

General formula (1)

wherein $R_1$, $R_2$ and $R_6$ each independently represent an alkyl group;

$R_3$ to $R_5$ each independently represent an alkyl group, or satisfy either of the following conditions i) and ii):

i) $R_3$ and $R_4$ are bonded to each other, so as to form a cyclic organic functional group containing $R_3$, $R_4$ and a carbon atom bonded simultaneously to $R_3$ and $R_4$, and $R_5$ represents an alkyl group; and ii) $R_3$ to $R_5$ are bonded to one another, so as to form a cyclic organic functional group containing $R_3$, $R_4$, $R_5$ and a carbon atom bonded simultaneously to $R_3$ to $R_5$; and $R_7$ and $R_8$ each independently represent an alkyl group or an acyl group, or $R_7$ and $R_8$ are bonded to each other, so as to form a cyclic organic functional group containing $R_7$, $R_8$ and a nitrogen atom bonded simultaneously to $R_7$ and $R_8$.

2. The coloring matter compound according to claim 1, wherein one of $R_7$ and $R_8$ of the general formula (1) is an alkyl group.

3. The coloring matter compound according to claim 1, wherein $R_3$ to $R_5$ of the general formula (1) each represent a methyl group.

4. An ink comprising:
the coloring matter compound according to claim 1; and
a medium for dissolving or dispersing the coloring matter compound therein.

5. The ink according to claim 4, wherein a content of the coloring matter compound is 1.0 to 30.0 parts by mass based on 100.0 parts by mass of the medium.

6. A resist composition for a color filter comprising the coloring matter compound according to claim 1.

7. A heat-sensitive transfer recording sheet, comprising: a substrate; and a coloring material layer formed on the substrate and containing the coloring matter compound according to claim 1.

* * * * *